Dec. 13, 1966 M. L. MEILLAND Plant Pat. 2,692
ROSE PLANT
Filed Oct. 12, 1965
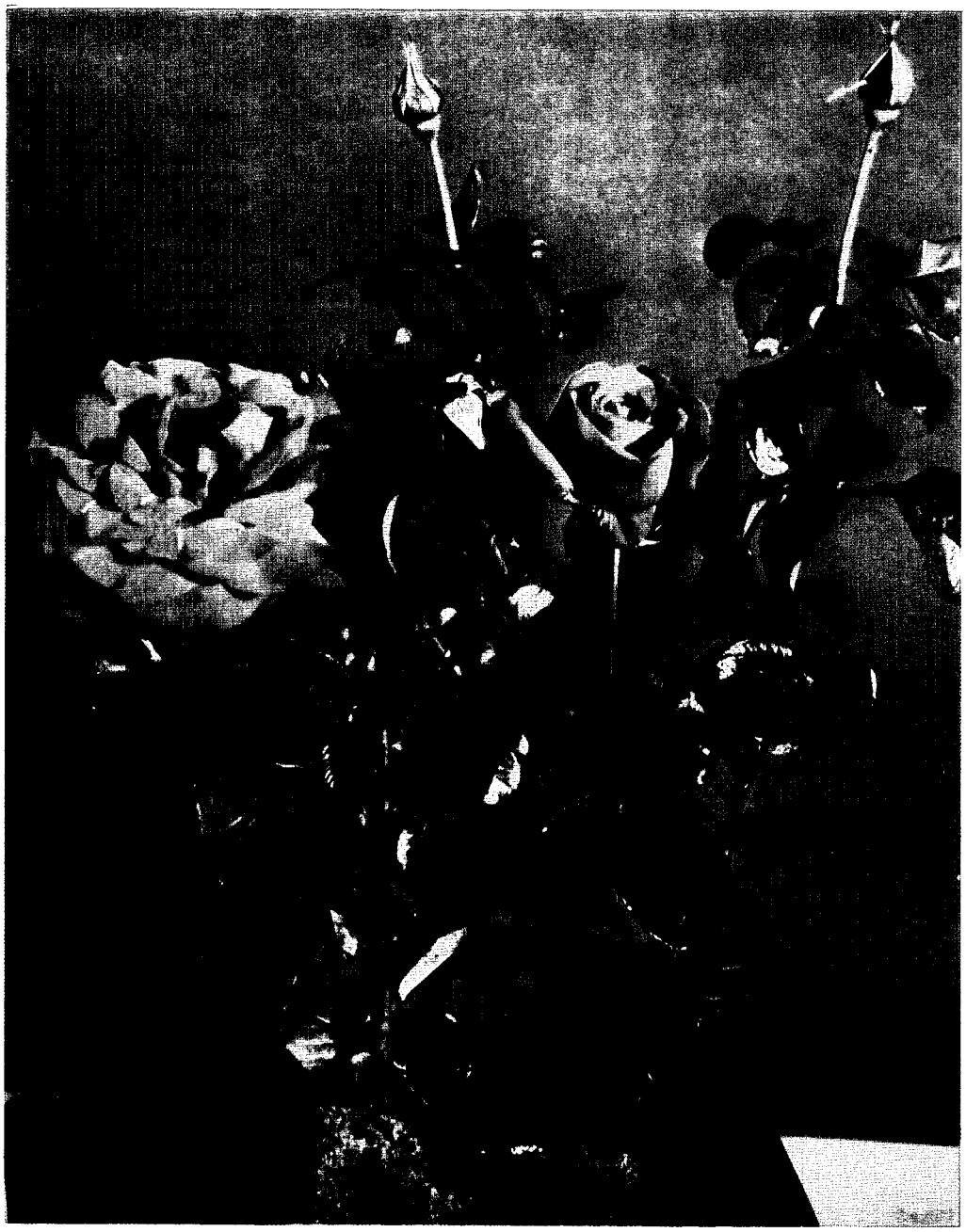
Inventor.
Marie Louise Meilland
By: Robb & Robb
Attorneys.

United States Patent Office

Plant Pat. 2,692
Patented Dec. 13, 1966

2,692
ROSE PLANT

Marie Louise Meilland, Alpes Maritimes, France, assignor to The Conard-Pyle Company, West Grove, Pa., a corporation of Pennsylvania Filed Oct. 12, 1965, Ser. No. 495,365
Claims priority, application France, Aug. 13, 1965, 46,314
1 Claim. (Cl. Plt.—21)

The present invention relates to a new and distinct variety of rose plant of the hydbrid tea class, which was orignated by me by crossing an unnamed and unpatented seedling of "Happiness" (U.S. Plant Patent No. 911)×"Independence" (U.S. Plant Patent No. 1,036) with the variety "Sutter's Gold" (U.S. Plant Patent No. 885), the unnamed seedling being the seed parent, and the variety "Sutter's Gold" being the pollen parent.

As the result of this breeding, I have produced a new and improved rose variety which is distinguished from its parents, as well as from all other varieties of which I am aware, as evidenced by the following unique combination of characteristics which are outstanding therein:

(1) A vigorous and well-branced habit of growth;

(2) A habit of producing flowers in clusters, as well as occasionally on single stems;

(3) Attractive bright green foliage of large size and oval shape as more particularly described and illustrated; and (4) A distinctive and attractive general color tonality of the flowers corresponding to what is generally described as dark, velvety, luminescent red.

No records or other information concerning the unnamed seed parent are available, and accordingly, no comparison of the new variety with this parent is possible.

In comparison with its pollen parent, "Sutter's Gold," the new variety has a more spreading plant habit; the buds are shorter; the flower petalage is usually slightly less, ranging from 25 to 30 petals or sometimes more, as compared with 30 to 35 petals which generally are typical of the flowers of "Sutter's Gold"; and the flower color is quite different, being a dark, velvety, luminescent red color, whereas the flowers of "Sutter's Gold" are a blend of yellow and red colors.

Asexual reproduction of the new variety of budding, as performed in France and also at West Grove, Pennsylvania, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hybrid tea.

Breeding: Seedling.

*Seed parent.*—An unnamed seedling of "Happiness"×"Independence."

*Pollen parent.*—"Sutter's Gold."

Propagation: Holds its distinguishing characteristics through succeeding propagations by budding.

*Flower*

Locality where grown and observed: West Grove, Pennsylvania, U.S.A.

Flowers borne: Sometimes singly and sometimes from 2 to several stem; on medium length to long stems of normal strength.

Quantity of bloom: Free, outdoors.

Continuity: Continuous.

Fragrance: Slight. Nature—tea.

Bud:

*Peduncle.*—Medium length; medium caliper; erect; stiff; rough; with medium number of reddish, glandular-tipped hairs. Color—green, sometimes overlaid with dull red.

*Before calyx breaks.*—Size—medium. Form—medium length; with a conspicuous neck; generally without foliaceous appendages on the surface of the bud; with bristle-like foliaceous parts extending beyond the tip of the bud equal to ½ or more of its length.

*As calyx breaks.*—Color—from Maroon, Plate 1030 to almost black.

*As first petal opens.*—Size—medium. Form—medium length; ovoid. Color: Outside—Ruby Red, Plate 827, with irregular blackish shadings; inside—between Rose Red, Plate 724 and Indian Lake, Plate 826, with occasional green vegetative streaks extending from the base to the margin.

*Opening.*—Opens up well.

Bloom:

*Size (when fully open).*—From medium to large; from 3¾ inches to 4¼ inches.

*Petalage.*—Double; from 25 to 30 petals and sometimes more; arranged regularly.

*Form.*—High-centered at first, but becoming shallow-cupped; petals being at first loosely rolled outward, and remaining loosely rolled outward at maturity.

Petals:

*Texture.*—Medium thickness; leathery.

*Appearance.* — Inside — satiny. Outside — shiny. Shape: Outer—round; intermediate—round; inner—undulate and irregular.

This description of a newly opended flower was made from a rose grown outdoors during the month of August at West Grove, Pennsylvania, U.S.A.:

*Color.*—Outer petals: Outside surface—Chrysanthemum Crimson, Plate 824/1, sometimes shaded with Maroon, Plate 1030; inside surface—Chrysanthemum Crimson, Plate 824, lightened by an underlying sheen of Cherry, Plate 722, and occasionally irregularly blotched with blackish shadings. Intermediate petals: Outside surface—Tyrian Purple, Plate 724; inside surface—Chrysanthemum Crimson, Plate 824, lightened by an underlying sheen of Cherry, Plate 722. Inner petals: Outside surface—Tyrian Purple, Plate 724; inside surface—Chrysanthemum Crimson, Plate 824, lightened by an underlying sheen of Cherry, Plate 722.

This description was made from a rose that was open for three days during the month of August at West Grove, Pennsylvania, U.S.A.:

*Color.*— Outer petals: Outside surface—Chrysanthemum Crimson, Plate 824/1; inside surface—Chrysanthemum Crimson, Plate 824, lightened by an underlying sheen of Cherry, Plate 722, and occasionally marked with blackish blotches. Inner petals: Outside surface—Rose Red, Plate 724; inside surface—Cardinal Red, Plate 822, lightened by an underlying sheen of Cherry, Plate 722.

*General color effect.*—Newly opened flower—Chrysanthemum Crimson, Plate 824, lightened by an underlying velvety sheen of Cherry, Plate 722. 3-days open—between Chrysanthemum Crimson, Plate 824 and Cherry, Plate 722, with velvety undertones.

*Behavoir.*—Drop off cleanly.

*Flower longevity.*—On bush in garden—5 days in August. Cut roses grown outdoors and kept at living room temperatures—5 days in August.

*Reproductive organs*

Stamens: Many; arranged regularly about pistils; mixed with petaloids.

Filaments: Most with anthers; medium length mixed with long. Color—pale yelow at base, becoming pink toward anthers.

Anthers: Open at various times; medium size; occasionally an anther fused with a petaloid. Color—pale yellow.

Pollen: Moderate quantity. Color—gold.

Pistils: Medium number.

Styles: Uneven; from short to medium length; medium caliper; bunched.

Stigma: Color—white, suffused with pink.

Ovaries: Some protruding from receptacle.

Hips: Medium length; globular; with inconspicuous neck; smooth; walls medium thick and fleshy. Color—green, becoming shaded with red.

Sepals: Permanent; long; straight; spear-shaped.

Seeds: Medium number; medium size.

*Plant*

Foliage:

*Leaves.*—Compound of 3, 5, and 7 leaflets; normal abundance; moderately large; leathery.

*Leaflets.*—Shape—oval, with apex acute. Base—obtuse. Margin—simply serrate.

*Color.*—Mature: Upper surface—Spinach Green, Plate 0960; under surface—Lavender Green, Plate 000761. Young: Upper surface—Maroon, Plate 1030, with occasional greenish undertones; under surface—near Pansy Purple, Plate 928/1, overlying green.

*Rachis (the supporting stem of the compound leaf).*—Medium caliper. Upper side—grooved; hairy; with occasional prickles along margin. Under side—sparsely prickly.

*Stipules.*—Medium length; medium width; with short points turning out at an angle of 45°.

*Disease resistance.*—Comparable to that of the average variety grown under the same cultural conditions at West Grove, Pennsylvania, U.S.A.

Growth:

*Habit.*—Bushy; upright; much-branched.

*Growth.*—Vigorous.

*Canes.*—Moderately heavy.

*Main stems.*—Dull. Color—Sage Green, Plate 000861. Prickles — several; color — brownish. Hairs—none.

*Branches.* — Dull. Color — Sage Green, Plate 000861, covered with a waxy bloom. Prickles—several; color—reddish-brown. Hairs—none.

*New shoots.*—Dull. Color—Fern Green, Plate 0862, overlaid with Pansy Purple, Plate 928/1. Prickles—several; color—purplish. Hairs—none.

I claim:

A new and distinct variety of rose plant of the hybrid tea class, substantially as herein shown and described, characterized particularly as to novelty by the unique combination of a vigorous and well-branched habit of growth, a habit of producing flowers in clusters, as well as occasionally on single stems, attractive bright green foliage of large size and oval shape as more particularly described and illustrated, and a distinctive and attractive general color tonality of the flowers corresponding to what is generally described as dark, velvety, luminescent red.

No references cited.

ABRAHAM G. STONE, *Primary Examiner.*

R. E. BAGWILL, *Assistant Examiner.*